United States Patent
Carlbark et al.

[19]

[11] Patent Number: 5,971,970
[45] Date of Patent: *Oct. 26, 1999

[54] ATTACHMENT BELT FOR ABSORBENT MATERIAL GARMENTS

[75] Inventors: Olle Carlbark, Kållered; Peter Rönnberg, Mölndal, both of Sweden

[73] Assignee: SCA Hygiene Products AB, Gothenburg, Sweden

[ * ] Notice: This patent issued on a continued prosecution application filed under 37 CFR 1.53(d), and is subject to the twenty year patent term provisions of 35 U.S.C. 154(a)(2).

[21] Appl. No.: 08/545,718
[22] PCT Filed: May 9, 1994
[86] PCT No.: PCT/SE94/00425
  § 371 Date: Nov. 7, 1995
  § 102(e) Date: Nov. 7, 1995
[87] PCT Pub. No.: WO94/26225
  PCT Pub. Date: Nov. 24, 1994

[30] Foreign Application Priority Data

May 12, 1993 [SE] Sweden .................................. 9301629

[51] Int. Cl.⁶ ...................................................... A61F 13/15
[52] U.S. Cl. ........................ 604/385.2; 604/391; 604/392
[58] Field of Search .............................. 604/385.1, 385.2, 604/386, 391, 392–402

[56] References Cited

U.S. PATENT DOCUMENTS

| | | |
|---|---|---|
| 4,964,860 | 10/1990 | Gipson et al. . |
| 5,066,289 | 11/1991 | Polski ....................................... 604/391 |
| 5,135,522 | 8/1992 | Fahrenkrug et al. .................... 604/392 |
| 5,151,092 | 9/1992 | Buell et al. ........................... 604/385.2 |
| 5,549,593 | 8/1996 | Ygge et al. .............................. 604/392 |

FOREIGN PATENT DOCUMENTS 1200177  7/1970  United Kingdom .

*Primary Examiner*—John G. Weiss
*Assistant Examiner*—K. M. Reichle
*Attorney, Agent, or Firm*—Burns, Doane, Swecker & Mathis, L.L.P.

[57] ABSTRACT

A belt for use with an absorbent garment generally for persons suffering from incontinence. The belt has two laterally spaced edges defining an area for releasable attachment of hook element strips of hook and loop type fastening elements. The belt also has only one defined portion, extending externally along a minor proportion of the length of the belt and across the major proportion of the width (z) of the belt, the defined portion being a non-attachment zone to which the hook elements cannot attach.

17 Claims, 4 Drawing Sheets

ATTACHMENT BELT FOR ABSORBENT MATERIAL GARMENTS

FIELD OF THE INVENTION

The invention relates to a belt for use with absorbent garments worn to assist in the collection of bodily discharges particularly for persons suffering from incontinence and, more particularly, the invention relates to a belt for use with an absorbent garment, said belt having two laterally spaced edges defining an area of material therebetween for releasable attachment of hook element strips of hook and loop type fastening means.

BACKGROUND TO THE INVENTION

Absorbent garments of the above mentioned type are well known in the art.

Two general types of belts for absorbent garments can primarily be identified. A first type is a belt attached integrally with the absorbent garment portion and a second type is a separate belt, to which an absorbent garment portion is attached by some means of releasable attachment, such as hook and loop (also called touch and close) type fastening means, for instance such as sold under the name VELCRO. The belt of the second type can be a disposable belt for limited use requiring no particular cleaning, or a more permanent type which may be washed several times before its effectiveness or appearance warrants a change to a new belt.

Published application WO-A-91/08725 discloses an example of both these general types in conjunction with an absorbent garment or "chassis" as it is sometimes referred to. Another example of a reusable belt is known for example from GB-A-2 242 612, whereby the belt is passed through slits in the absorbent lining and presents a hook and loop type mechanical fastener having both a hook part and a loop part of said fastener at either end of the belt.

One of the problems recognised with such garments is achieving maximum comfort for the user by correct fitting of the garment. Incorrect fitting will result in sore, cut and/or painful areas for the user. This is particularly the case if the users are unable to assist themselves or otherwise unable to communicate the fact to the assistant personnel.

A solution to this problem is proposed in the aforementioned WO-A-91/08725, whereby a separate belt worn by the user is provided with visual markings or targeting indicia whereby the centreline of the belt becomes more apparent and/or provides a location site for attachment for the hook element strips provided on the chassis portion.

Where the problem of incontinence is involved, it will be appreciated that persons suffering from this problem are often old and have physical handicaps of various types. As a consequence, they often require the assistance of personnel for fitting the garments. Due to the fact that many users of such belts are also bed-ridden and often heavy, the assistant personnel regularly have difficulties in fitting and attaching the garment to the wearer in a comfortable manner since dexterity (for positioning) and strength (for maneuvring the wearer) of the assistant are required simultaneously.

Moreover, the desired attachment points for the garment (i.e. of the chassis to a separate belt) such as the indicia disclosed in the aforementioned WO-A-91/08725 are often not visible or easily visible, such as in the case of a bed-ridden user where attachment of the chassis will occur underneath or behind the user.

Thus there is a need for a solution which allows easy and correct fitting of the garment, particularly in the case of bed-ridden persons.

Further objects of the invention will become apparent to the reader in the course of reading the following description of certain preferred embodiments.

SUMMARY OF THE INVENTION

The aforementioned problems relating to fitting and comfort when wearing absorbent garments of the aforementioned type are solved by the features of the belt of the present invention, as recited in claim 1, with the preferred features of the belt being defined in the dependent claims.

As a consequence of the use of the non-attachment zone of the present invention, the fitting of the hook element strips of a chassis to be attached is facilitated without the requirement, for instance, of being able to see the attachment zones, since the person fitting the absorbent garment to the belt is only able to attach the hook element strips of the chassis in substantially the correct locations, which lie just outside either edge of the zone of non-attachment.

It should be noted that, whilst the term absorbent garment has been used particularly in conjunction with incontinence, and particularly adult incontinence, the invention is not limited to this particular use or any particular size or type of absorbent garment implied thereby and it is clear for the skilled man that such belts could be used with baby's or children's nappies (diapers) for example, merely by adapting the dimensions appropriately.

BRIEF DESCRIPTION OF THE DRAWINGS

The invention will now be explained in more detail with reference to certain non-limiting embodiments and with reference to the accompanying drawings, in which.

DETAILED DESCRIPTION OF PREFERRED EMBODIMENTS

Figure 1:
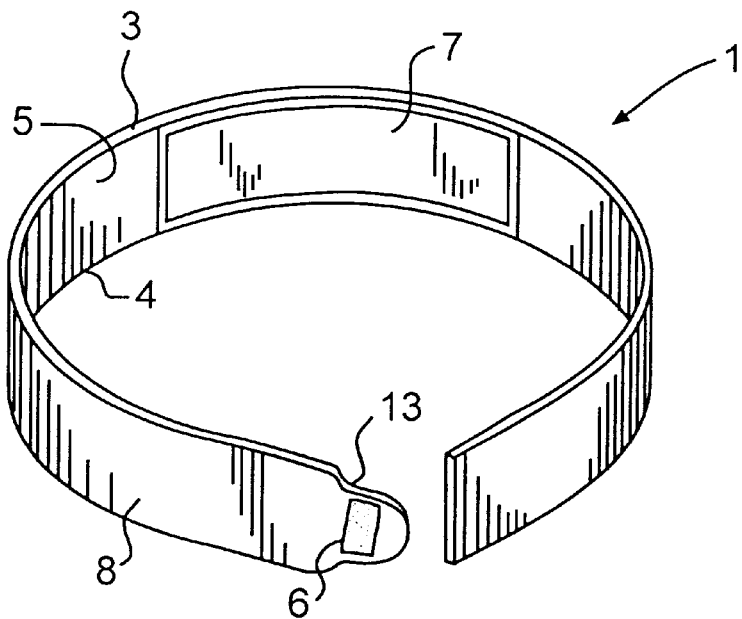
FIG. 1 depicts a belt in accordance with the invention whereby, for purposes of clarity, the belt is shown looped in the opposite manner to that obtained upon wearing.

FIG. 1 shows a belt generally denoted 1 which is made of flexible material such that it can be wrapped around a user's waist. The belt in FIG. 1 is shown, for reasons of clarity, wrapped around an imaginary centre point in a manner opposite to that normally used when fitted to a user. Thus the inside of the belt 8 is here shown as if it were on the outside.

Figure 4:
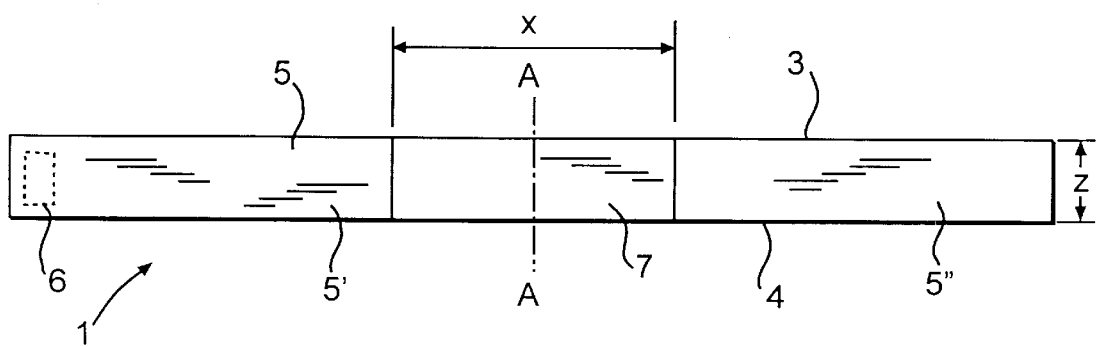
FIG. 4 shows a belt according to the invention laid out flat.

The belt is substantially rectangular in shape comprising two laterally spaced longitudinal edges 3 and 4 separated by a distance z (see FIG. 4). At one end, the belt is foreseen with an end portion 13 here shown as having a reduced width, on which end portion is securely affixed a flexible strip 6 having hook elements. This hook element strip is of the type forming one half of the joining portions of a hook and loop type fastening means. The loop part of the joint in the embodiment shown is formed by the belt material itself.

Figure 3:
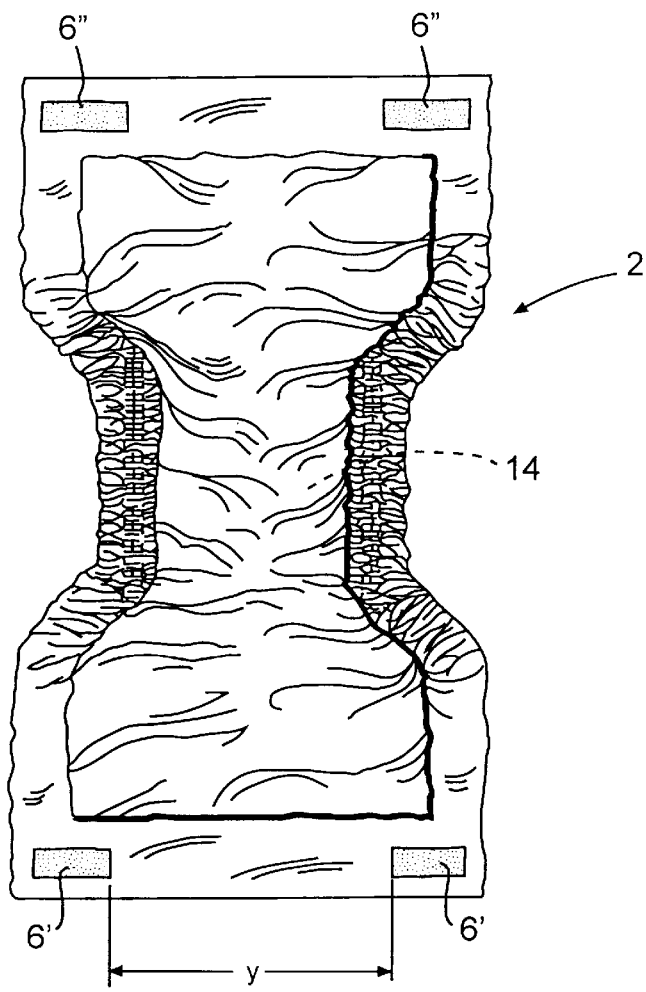
FIG. 3 shows an absorbent garment in the form of a chassis, adapted for fitting to the belt of the invention.

The outside of the belt 5 (depicted in FIG. 1 as the inside) serves as an area of releasable attachment, partly for the strip 6 located at one end of the belt and also for similar strips 6' and 6" of a chassis 2 having absorbent material 14 therein (see FIG. 3).

On the outside surface 5 of the belt 1 there is a defined portion 7, formed by a strip of suitable material on the outside surface 5 of the belt, to which the hook element strips 6' and 6" cannot attach. This area 7 thus forms a zone of non-attachment and as depicted has its centreline substantially common with the centreline A—A of the main belt portion. The zone 7 extends either entirely across the width of the belt or at least across a major proportion thereof. By "major proportion" is hereby meant more than 50%, although the actual extent across the width of the belt will generally be such that it would be impossible for the strips 6' and 6" to be able to attach themselves to sufficient surface 5 above or below the longer edges of the area 7. The non-attachment zone 7 also extends along a minor proportion of the belt, i.e. along less than 50% of the total belt length. Most normal belts for use in this field are no longer than 150 cm such that the maximum length of zone 7 would normally be no more than about 70 cm, although as little as 5 cm is possible depending on the length of the belt and the size of the garment 2 to be attached. Preferably, however, the length of zone 7 lies between 25 and 40 cm in the case of adult incontinence applications.

Whilst the zone 7 is generally formed by adding a piece of material (to which hook elements will not attach, e.g. a plastic material) to an existing belt of material suitable for releasable attachment of hook elements, it is clearly also feasible that the main body of the belt may be formed entirely, or to a large extent, by the material of the non-attachment zone. In order to provide attachment zones as claimed it is then necessary to attach two lengths or strips 5' and 5" of belt material suitable for releasable attachment thereto of hook elements, such that the inner margins of said strips define the start and end of the zone of non-attachment.

The manner of fitting a chassis 2 to the belt 1 will now be described. Firstly the belt is passed around the wearer's waist and the hook element strip 6 is pressed lightly onto the releasable attachment surface 5 to fasten it in place. The zone 7 will be facing outwardly and positioned approximately with its centreline in line with the wearer's spinal column (i.e. approximately central with regard to the wearer's back). The chassis portion is then attached to the outside of the belt behind the wearer's back by attaching the two strips 6' (or alternatively strips 6") to the belt surface 5.

The distance y between the inner margins of the strips 6' or 6" is greater than the length x of the zone 7. Thus the two strips 6' or 6" can easily be located on the correct areas of the belt, since these are the areas where both strips 6' (or 6") attach. The other end of the chassis (i.e. the end not yet attached) is then passed through the legs of the wearer and attached to the front of the belt.

The result for the patient is that the chassis is positionally correctly fitted which means not only that the chassis does not exert a sideways pulling force on the legs or crotch due to incorrect placement, but also that no twisting of the belt is induced, which itself can be a cause of cutting and soreness.

Figure 7:
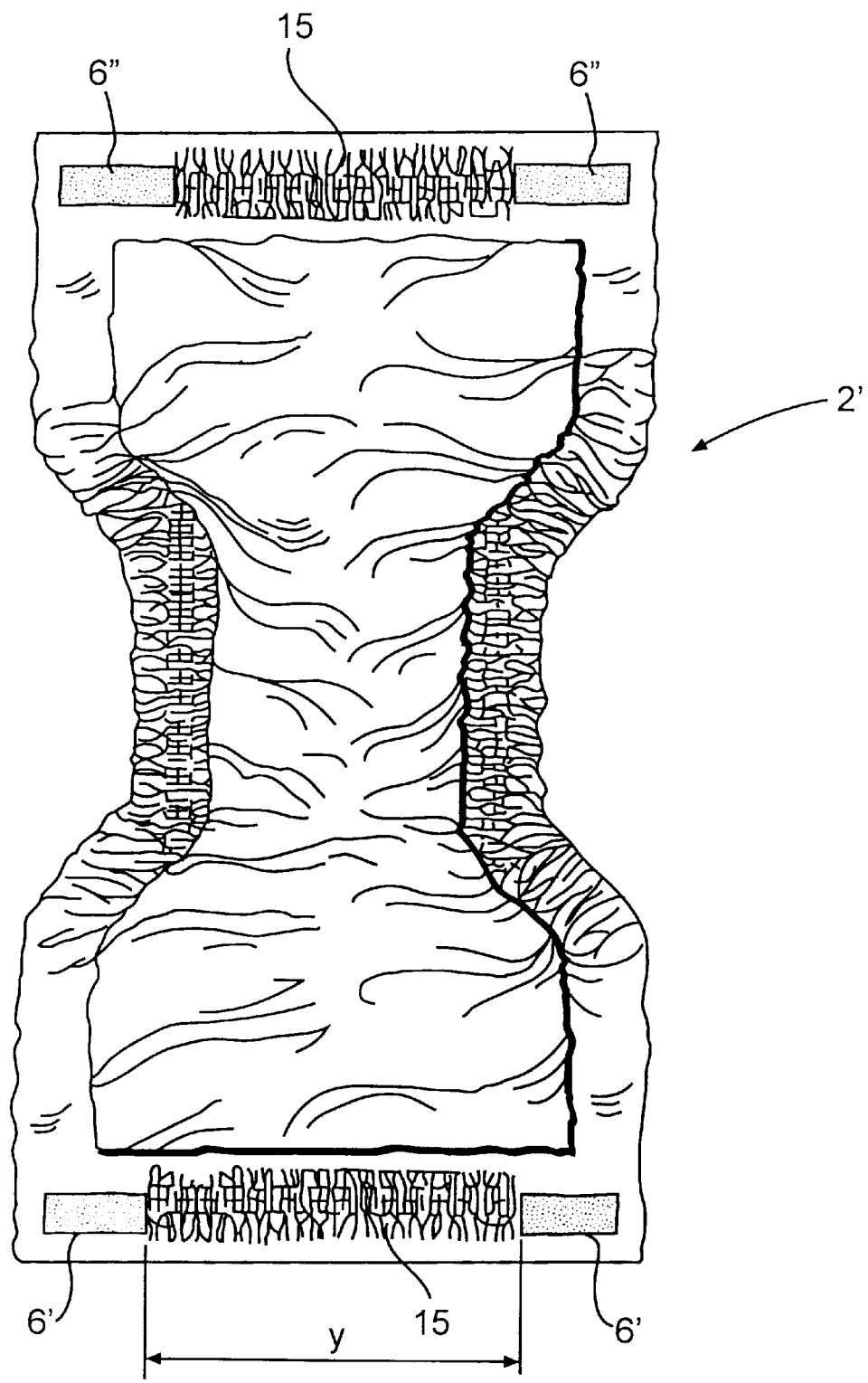
FIG. 7 depicts an alternative embodiment of the absorbent garment shown in FIG. 3.

Whilst less preferable, the chassis 21 may have the strips 6' or 6" located on an elasticated or extendable portion 15. Fitment of the chassis correctly then requires merely extending the strips 6' away from each other until they have a separation y greater than the length x of the zone 7 as shown in FIG. 7.

Figure 2:
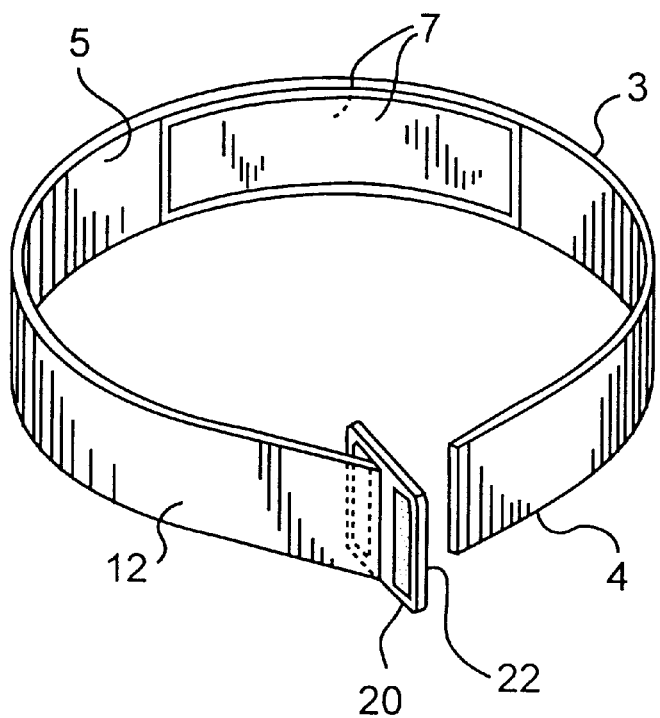
FIG. 2 depicts a belt according to the invention wherein the belt is of the reversible type, capable of being used either way round.
Figure 5:
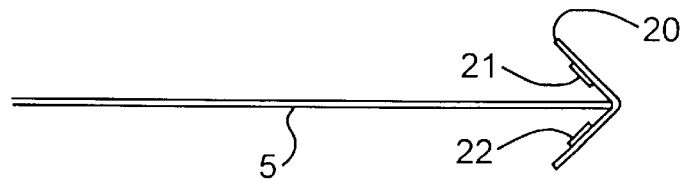
FIG. 5 shows a plan view of a reversible belt similar to that in FIG. 2.

A further embodiment of the invention is shown in FIG. 2 and FIG. 5 which show a reversible belt, i.e. a belt which can be used either way round since both sides are substantially identical. In accordance with the invention the belt is thus provided with corresponding zones 5 and 12 for releasable attachment on either side and with a non-attachment zone 7 on either side.

It will be understood that the use of a reversible belt in its own right, even without any zone 7, presents significant advantages over prior known belts having one-sided use only, since there is no requirement when fitting the belt to check which side of the belt is the outside. This is of significant advantage in the dark or for wearers who are partially or totally blind for example.

At one end of the belt there is attached (by welding or other means) an extra material piece 20, which is made of a flexible material and which has attached thereto two strips 21 and 22 of hook elements. Depending on which way round the belt is worn, either one or the other hook element strip 21 or 22 can be used for fastening the belt.

Generally, the strips 7 on either side of the belt will be the same size, although it is possible that they could be of different size. This might for example be useful where it is desired to have a smaller, less bulky and thus less visible chassis during the day and a bulkier one at night, whereby the distance apart "y" of the strips 6' for example might be different.

Clearly advantageous with the use of such belts of the single sided type is where the inner surface material of the belt is made either partially or entirely of absorbent, thus absorbing perspiration for example. This then allows freedom of choice of the material for the outside of the belt in the releasable attachment area 5.

A woven material is normally used for both sides of the belt, due to its releasable attachability characteristics for hook element strips and also due to its washability.

However it is now possible even to use non-woven, cheaper materials for the outside of the belt due to the development of a hook element strip having releasable attachability to non-woven materials. Thus, since non-woven materials are not easily washable without causing wrinkles for example, it is a possibility to use an absorbent material, possibly also a non-woven material, for the inner surface of such a belt if the belt is to be a disposable one (i.e. not designed for re-use after washing). Thus, it is possible to have an outer side surface and an inner side surface made from a non-woven material, and it is possible to achieve a belt which is cheap and disposable after limited use with a small number of chassis.

In particular, when using non-woven materials for the releasable attachment surface or area 5 (FIG. 1) or 5, 12 (FIG. 2) of the belt it is possible to achieve particularly favourable peel strength and shear strength combinations, which give a peel strength of $0.1–2.0$ $Ncm^{-1}$, preferably down to as low as $0.2–0.8$ $Ncm^{-1}$, and a shear strength greater than 1 $Ncm^{-2}$, preferably greater than 15 $Ncm^{-2}$ and normally greater than 20 $Ncm^{-2}$.

Since comfort of the wearer is a particularly important consideration in this field and in particular to fitting of the belt, it has been shown advantageous to adopt a particular placement of the hook element strips for fastening the belt together. Thus in order to reduce, to a great extent the possibility of the hook element strips contacting the wearer's waist due to incorrect fitting of the belt, or for the case where the waist of the user increases dimension, the hook element strip or strips are made of such a length and width and are positioned with such an orientation so as to avoid this.

Figure 6A:
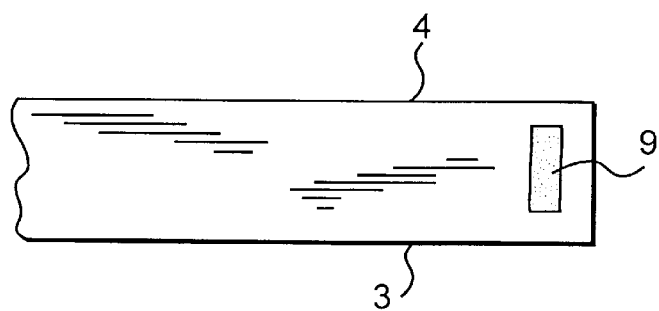
FIG. 6(A) shows a first embodiment of elongate hook element strips applied to the belt of the present invention.
Figure 6B:
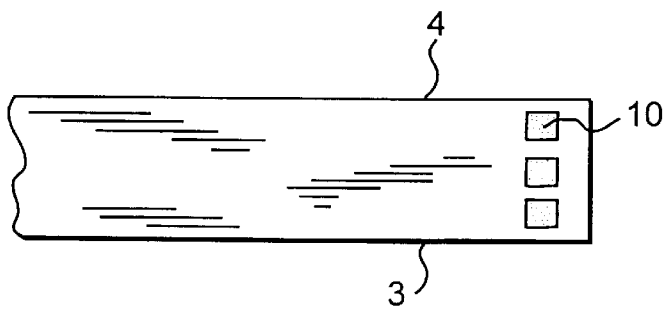
FIG. 6(B) shows a second embodiment of elongate hook element strips applied to the belt of the present invention.
Figure 6C:
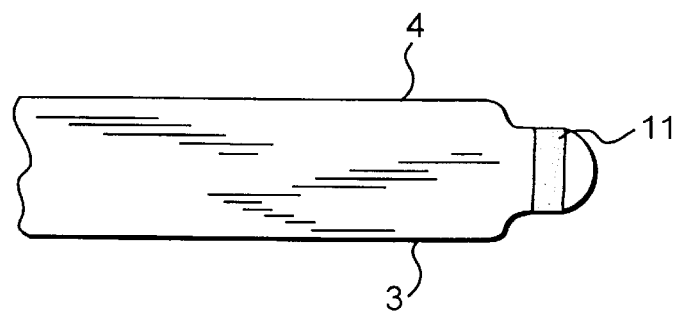
FIG. 6(C) shows a third embodiment of elongate hook element strips applied to the belt of the present invention.

As can be seen from FIGS. 6(A)–(C), showing three possible strip embodiments 9, 10, and 11 the distance between the outer edges of the strip(s) is placed at a distance from each edge 3, 4 of the belt. In this way, when the belt is fitted, if slightly angled or not correctly overlapped, the hook elements will not project beyond the edge of the belt and thus will not contact the wearer's body.

As can be seen, the strips are generally elongate, or in the case of a series of strips 10 as in FIG. 6(B), the series of strips is elongate. Preferably a ratio of greater than 2:1 elongation is used and even more preferably an elongation ratio of over 3:1. Thus to achieve the aforementioned advantages it is preferable to lay the strips with their larger dimension across the belt width, as depicted, and to give the strips a dimension such that the larger dimension has a length of between 25% and 75% of the width (z) of the main area (5) of the belt. By width of the belt, is hereby meant the width of the belt at the zone where the strip 9, 10, 11 will attach. Thus in the embodiment of FIG. 6(C), although the strip 11 extends entirely across the reduced portion of the belt, the strip still lies within the stated range. In particular it has been found particularly advantageous to use a strip with a length which is less than 60%. Due to the shear strength which can be achieved by the use of non-woven materials as the belt attachment surface, it is also easy to acquire adequate shear strength with only minimal attachment area.

Whilst particular embodiments of the invention have been described above, it is to be understood that these are in no way limiting for the scope of the invention which is defined by the scope of the claims appended hereto.

What is claimed is:

1. A belt for use with an absorbent garment, said belt comprising:
    a belt member having two laterally spaced edges, a first side surface, a second side surface, and two opposing ends;
    said belt member further including a main area of material extending between said spaced edges consisting of attachment portions for releasable attachment of hook element strips of hook and loop fastening means and only one defined portion to which the hook element strips will not attach, said one defined portion extending externally along a minor proportion of a length of the belt member and across a major proportion of a width of the belt member,
    wherein said one defined portion is disposed approximately centered between said two opposing ends of said belt member, said one defined portion being located with a centreline thereof approximately in line with a centreline of the belt member as defined between said two opposing ends.

2. A belt according to claim 1, wherein said one defined portion is formed by a piece of additional material attached to said main area of the belt member.

3. A belt according to claim 1, wherein said attachment portions being further constituted by two material strips, an inner edge of each material strip being attached to the main area of material, such that a distance between the inner edges of the two material strips thus forms said one defined portion.

4. A belt according to claim 1, wherein said first and second side surfaces of the belt member are substantially identical such that the belt is reversible.

5. A belt according to claim 4, wherein one end of the belt is provided with a further piece of material having a first and a second end, said piece of material having hook element strips attached thereto at the first and second ends thereof.

6. A belt according to claim 1, wherein said attachment portions are disposed on the first side surface of the belt member, and the second side surface of the belt member being made at least partially of an absorbent material.

7. A belt according to claim 1, wherein one end of the belt member includes a hook element attachment strip for securing the belt to itself around a user, said strip being elongated with its larger dimension having a length of between 25% and 75% of the width of the belt member, said larger dimension laying substantially in a width direction of the belt member.

8. A belt according to claim 1, wherein at least said attachment portions are made from a non-woven material.

9. A belt according to claim 8, wherein said first and second side surfaces of the belt are made from non-woven material.

10. A belt according to claim 1, wherein a length of said one defined portion lies between 5 and about 70 cm.

11. A belt according to claim 10, wherein the length of said one defined portion lies between 25 and 40 cm.

12. An absorbent garment system including a belt according to claim 1, said absorbent garment system further comprising an absorbent garment including an absorbent attachment part having a plurality of opposing strips of hook elements secured thereto at opposing ends thereof, inner margins of said opposing strips at one of the opposing ends being spaced apart by a predetermined distance such that the strips at the one of the opposing ends, when fitted correctly to the belt, lie outside an outer edge of said one defined portion.

13. An absorbent article system according to claim 12, wherein the strips at the one of the opposing ends lie on an elasticized portion of the attachment part such that, when stretched, the inner margins of said opposing strips at the one of the opposing ends can be spaced by a distance greater than a length of said one defined portion.

14. An absorbent garment system according to claim 12, wherein said attachment portions consist of a non-woven material and wherein a connection between the hook element strips of the attachment part to the belt each have a peel strength of 0.1–2.0 Ncm$^{-1}$ and a shear strength greater than 1 Ncm$^{-2}$.

15. An absorbent garment according to claim 14, wherein the connection between the hook element strips of the attachment part to the belt each have a peel strength of 0.2–0.8 Ncm$^{-1}$.

16. An absorbent garment according to claim 14, wherein the connection between the hook element strips of the attachment part to the belt each have a shear strength greater than 15 Ncm$^{-2}$.

17. An absorbent garment system comprising:
    (a) a belt having two laterally spaced edges, a first side surface, a second side surface, and two opposing ends;
    said belt further including a main area of material extending between said spaced edges consisting of attachment portions for releasable attachment of hook element strips of hook and loop fastening means and only one predetermined portion to which hook element strips will not attach, said one predetermined portion extending externally along a minor proportion of a length of the belt and across a major proportion of a width of the belt; and (b) an absorbent garment having at least one absorbent attachment area including a plurality of strips of hook elements secured thereto at opposing ends thereof, inner margins of said strips at one of the opposing ends being spaced apart by a predetermined distance such that said strips at the one of the opposing ends, when fitted correctly to said belt, lie on opposing sides of said one predetermined portion.

* * * * *